US009579297B2

(12) United States Patent
Ishima et al.

(10) Patent No.: US 9,579,297 B2
(45) Date of Patent: Feb. 28, 2017

(54) PHARMACEUTICAL COMPOSITION FOR APPLICATION TO NAIL

(75) Inventors: Tomohiro Ishima, Yokohama (JP); Mamoru Naruse, Higashikagawa (JP); Hideo Kaneda, Kawachinagano (JP); Kazuo Kanai, Chuo-ku (JP); Takashi Sekine, Inashiki (JP); Shinichi Ota, Kashiwa (JP); Tomonari Yoshimura, Inashiki-gun (JP)

(73) Assignee: TEIKOKU SEIYAKU CO., LTD., Higashikagawa-shi, Kagawa (JP)

( * ) Notice: Subject to any disclaimer, the term of this patent is extended or adjusted under 35 U.S.C. 154(b) by 1052 days.

(21) Appl. No.: 12/159,591

(22) PCT Filed: Dec. 26, 2006

(86) PCT No.: PCT/JP2006/325842
§ 371 (c)(1),
(2), (4) Date: Jun. 27, 2008

(87) PCT Pub. No.: WO2007/077806
PCT Pub. Date: Jul. 12, 2007

(65) Prior Publication Data
US 2009/0202602 A1 Aug. 13, 2009

(30) Foreign Application Priority Data
Dec. 28, 2005 (JP) ................. 2005-378441

(51) Int. Cl.
*A61K 31/00* (2006.01)
*A61F 13/10* (2006.01)
*A61K 9/70* (2006.01)
*A61K 31/4178* (2006.01)
*A61K 45/06* (2006.01)
*A61F 13/00* (2006.01)

(52) U.S. Cl.
CPC ............ *A61K 31/00* (2013.01); *A61F 13/105* (2013.01); *A61K 9/7061* (2013.01); *A61K 31/4178* (2013.01); *A61K 45/06* (2013.01); *A61F 2013/00906* (2013.01)

(58) Field of Classification Search
CPC .... A61K 31/00; A61K 31/4178; A61K 45/06; A61F 13/105; A61F 2013/00906; A61F 9/7061
See application file for complete search history.

(56) References Cited

U.S. PATENT DOCUMENTS

| 3,932,653 A | 1/1976 | Stoughton |
| 4,983,385 A | 1/1991 | Hasegawa et al. |
| 5,160,743 A | 11/1992 | Edgren et al. |
| 6,143,793 A | 11/2000 | Laugier et al. |
| 6,207,184 B1 | 3/2001 | Ikeda et al. |
| 2003/0170308 A1* | 9/2003 | Cleary et al. ............... 424/486 |
| 2003/0235541 A1* | 12/2003 | Maibach et al. ............. 424/61 |
| 2004/0247657 A1 | 12/2004 | Susilo |

FOREIGN PATENT DOCUMENTS

| GB | 2 202 743 A | 10/1988 |
| JP | 58-162514 A | 9/1983 |
| JP | 63-258814 | 10/1988 |
| JP | 1-501143 A | 4/1989 |
| JP | 5-85929 A | 4/1993 |
| JP | 9-504510 | 5/1997 |
| JP | 9-504536 A | 5/1997 |
| JP | 9-504537 A | 5/1997 |
| JP | 10-152433 | 6/1998 |
| JP | 10-226639 A | 8/1998 |
| JP | 2002-537317 A | 11/2002 |
| JP | 2003-252798 A | 9/2003 |
| JP | 2004-83439 A | 3/2004 |
| JP | 2004-529923 A | 9/2004 |
| JP | 2005-503318 A | 2/2005 |
| JP | 2005-529901 A | 10/2005 |
| WO | 87/02580 A1 | 5/1987 |
| WO | 95/03775 A1 | 2/1995 |
| WO | 95/12393 A1 | 5/1995 |
| WO | 95/12397 A1 | 5/1995 |
| WO | 00/50007 A1 | 8/2000 |
| WO | 01/60325 A1 | 8/2001 |
| WO | 02/083084 A1 | 10/2002 |
| WO | 03/092650 A1 | 11/2003 |
| WO | 2004/032902 A1 | 4/2004 |

OTHER PUBLICATIONS

Yoichi Kobayashi, et al, "Tsume Hakusen to Yakubutsu Toka—Tsume Mizumushi Wa Nurigusuri De Naorunoka—" Pharmacia, 1999, pp. 569-573, vol. 35.
Dirk Mertin, et al, "In-Vitro Permeability of the Human Nail and of a Keratin Membrane From Bovine Hooves: Prediction of the Penetration Rate of Antimycotics Through the Nail Plate and Their Efficacy", Journal of Pharmacy and Pharmacology, 1997, pp. 866-872, vol. 49, No. 9.
Antje S. Uch, et al, "Use of 1-Methyl-Pyrrolidone as a Solubilizing Agent for Determining the Uptake of Poorly Soluble Drugs", Pharmaceutical Research, 1999, pp. 968-971, vol. 16, No. 6.
Jong-Yun Kim et al. "Rheological properties and microstructures of Carbopol gel network system," Colloid & Polymer Science, 2003, v. 281, pp. 614-623, Korea.
Hennink, W.E. and Van Nostrum, C.F., "Novel crosslinking methods to design hydrogels," Advanced Drug Delivery Reviews, v. 54, pp. 13-36 (2002).
Extended European Search report dated Nov. 14, 2012, issued in European Patent Application No. EP 06 84 3226.
Sen et al., "Dynamic deswelling studies of poly(N-vinyl-2-pyrrolidone/itaconic acid) hydrogels swollen in water and terbinafine hydrochloride solutions", Eur. Polymer J., vol. 38, vol. 38, No. 4, pp. 751-57 (Apr. 1, 2002).
Sen et al., "Controlled release of antifungal drug terbinafine hydrochloride from poly(N-vinyl 2-pyrrolidone/itaconic acid) hydrogels," Int. J. Pharma., vol. 228, No. 1-2, pp. 33-41 (Oct. 9, 2001).
Office Action issued Sep. 11, 2012 in Japanese Patent Application No. 2007-552927.

* cited by examiner

*Primary Examiner* — Kyle Purdy
(74) *Attorney, Agent, or Firm* — Sughrue Mion, PLLC

(57) ABSTRACT

Since treatment effects of conventional external preparations were not satisfactory, it is aimed to provide a novel external preparation that is excellent in drug permeability to nail, capable of fully exhibiting effects of an antifungal drug, and effective for treatments of diseases such as nail mycosis and nail candidiasis, particularly, treatments for nail tinea. The external preparation of this invention is a pharmaceutical composition for nail characterized by containing an antifungal drug, alkylpyrrolidone or a derivative thereof, and a crosslinking hydrogel.

2 Claims, 2 Drawing Sheets

PHARMACEUTICAL COMPOSITION FOR APPLICATION TO NAIL

TECHNICAL FIELD

This invention relates to a pharmaceutical composition for nail that is capable of fully exhibiting effects of an antifungal drug and excellent in permeability to nail.

RELATED ART

Nail tinea (onychomycosis) is one of fungal infections and known as an intractable disease. A treatment with an external preparation or an oral preparation is performed as a treatment method for the nail tinea at present, and, since there are many patients who cannot be treated with the oral preparation due to problems of adverse side effects and drug interaction of the treatment with oral preparation, such patients are treated with the external preparation. However, since commercially available external preparations have low permeability to nail, any satisfactory treatment effect has not been attained in the present situation. From the reason of easy application to the nail, film forming type compositions such as a nail lacquer and a manicure type preparation have been investigated as therapeutic preparations for nail mycosis.

However, since a water-insoluble film forming agent is used as a film forming substance for such film forming type compositions in order to achieve film strength and water resistance, there have been problems of discharge of the antifungal drug from the film formed on the coating surface and insufficient permeability to nail. Further, there has been another problem that the nail is dehydrated by organic agents such as acetone, ethyl acetate, and toluene contained in the composition to be hardened, resulting in reduction in permeability of the antifungal drug to the nail.

On the other hand, a film forming antifungal drug composition containing a hydrophilic film forming substance, an antifungal drug, and water has been known (Patent Document 1). However, since a water content of the composition is low, which is 3% to 10% of the whole composition, drug-permeability to nail of the composition is low. Therefore, it is difficult to allow the antifungal drug to permeate into the nail by the composition, resulting in unsatisfactory exhibition of the effects of the antifungal drug.

Also, Tsuboi et al. have reported that a method of hydrating a nail by employing a tightly-sealing therapy wherein: an antifungal cream containing 40% of urea is prepared; the cream is applied on the nail; and the nail is covered with a polyvinyl chloride film has efficacy (Non-Patent Document 1). However, in view of stability of the cream containing urea in the amount of 40% and complication of the treatment method, the treatment method is not exactly versatile.

Further, since the nail plate has a considerably low content of a lipid component that influences on the drug-permeability as compared to the skin horny layer, it is difficult to employ an ordinary technology of antifungal drug for skin as it is for a therapeutic drug for nail plate, and that it is noted that water-solubility of a drug must be increased in order to effectively conduct a drug treatment on the nail tinea. (Non-Patent Document 2).

As a technology for increasing water-solubility of drug, there has been known an antifungal external preparation for nail containing a hydrochloride salt and a basic substance, in which the hydrochloride salt is obtained from slightly water-soluble neticonazole to increase water-solubility (Patent Document 2). However, since not every antifungal drug is increased in water-solubility by the transformation into hydrochloride salt, the method is not a versatile method.

As a technology of using a slightly water-soluble antifungal drug for a therapeutic preparation for nail plate, there has been known a method wherein a pre-treatment liquid containing ethanol, water, and N-methylpyrrolidone is applied on a nail plate to enhance drug-permeability, and then a composition for nail containing a gel base and fluconazole, which is an antifungal drug, is applied on the nail plate (Patent Document 3). However, this method is complicated since it is necessary to conduct two drug applications, and the pre-treatment liquid used in the method has a problem of storage stability due to its high ethanol content.

Also, a composition obtained by dissolving griseofulvin, which is a slightly water-soluble antifungal drug, into N-methyl-2-pyrrolidone has been known (Patent Document 4). However, this composition has a problem in terms of stability and irritating property due to organic solvents such as ethanol and acetone or N-methyl-2-pyrrolidone contained at a high concentration.

Patent Document 1: JP-A-10-152433
Patent Document 2: JP-A-2004-83439
Patent Document 3: JP-A-2004-529923
Patent Document 4: U.S. Pat. No. 3,932,653
Non-Patent Document 1: Japanese Journal of Medical Mycology, vol. 39, 11-16, 1998.
Non-Patent Document 2: Pharmacia, vol. 35, 569-573, 1999.

DISCLOSURE OF THE INVENTION

Problems to be Solved by the Invention

Since the therapeutic effects of the conventional external preparations for nail have not been satisfactory as described in the foregoing, there has been a demand for development of a novel external preparation for nail mycosis, which is excellent in drug-permeability to nail and capable of fully exhibiting effects of an antifungal drug, and an object of this invention is to provide such external preparation.

Means for Solving the Problems

The inventors had conducted extensive research in order to solve the above-described problems and found that a pharmaceutical composition for nail containing alkylpyrrolidone or a derivative thereof and a crosslinking hydrogel is excellent in drug-permeability to the nail and capable of fully exhibiting effects of an antifungal drug, and that a use of the pharmaceutical composition for nail as an adhesive patch enhances convenience, thereby accomplishing this invention.

Specifically, this invention provides a pharmaceutical composition for mail characterized by comprising an antifungal drug, alkylpyrrolidone or a derivative thereof, and a crosslinking hydrogel.

Also, this invention provides an adhesive patch for nail obtainable by applying and spreading the above-described pharmaceutical composition for nail on a support.

Effect of the Invention

The pharmaceutical composition for nail of this invention is capable of enhancing drug-permeability to nail and fully exhibiting effects of an antifungal drug. Also, the pharmaceutical composition for nail of this invention enables stable drug retention in long term storage since the pharmaceutical composition for nail does not contain ethanol and the like.

Therefore, the pharmaceutical composition for nail of this invention is expected to be used as an external preparation that is effective for treatments of nail tinea and the like.

Best Mode for Carrying out the Invention

The pharmaceutical composition for nail of this invention contains as essential ingredients an antifungal drug, alkylpyrrolidone or a derivative thereof, and a crosslinking hydrogel.

Examples of the antifungal drug to be used for the pharmaceutical composition for nail of this invention includes an azole-based antifungal drug such as lanoconazole, bifonazole, neticonazole, croconazole, clotrimazole, ketoconazole, iconazole, econazole, oxiconazole, sulconazole, miconazole, isoconazole, thioconazole, fluconazole, itraconazole, and luliconazole; an allylamine-based antifungal drug such as terbinafine; a benzylamine-based antifungal drug such as butenafine; a thiocarbamic acid-based antifungal drug such as tolnaftate; a morpholine-based antifungal drug such as amorolfine; a polyene macrolide-based antifungal drug such as nystatin; other antifungal drugs such as undecylenic acid, salicylic acid, ciclopirox olamine, siccanin, tolciclate, mokutar, liranaftate, pyrrolnitrin, griseofulvin, naftifin, and exalamide; pharmacologically acceptable salts thereof; and the like.

In this invention, slightly water-soluble antifungal drugs are preferred among the above antifungal drugs, and specific examples of the slightly water-soluble antifungal drugs include lanoconazole, bifonazole, neticonazole, cloconazole, clotrimazole, ketoconazole, iconazole nitrate, econazole nitrate, oxiconazole nitrate, sulconazole nitrate, miconazole nitrate, isoconazole nitrate, thioconazole, fluconazole, itraconazole, terbinafine hydrochloride, butenafine hydrochloride, tolnaftate, amorolfine hydrochloride, and nystatin. Among these slightly water-soluble antifungal drugs, it is particularly preferable to use lanoconazole, bifonazole, terbinafine hydrochloride, butenafine hydrochloride, amorolfine hydrochloride, and the like since they have wide antifungal spectrum and high antibacterial activity. As used herein, slightly water-soluble means a characteristic of being much more hardly soluble to water than the degree that is considered hardly soluble when evaluating solubility to water in accordance with the solubility evaluation method in the column of properties of Japanese Pharmacopoeia, i.e. solubility to water of 0.01 g/mL or less.

A content of the antifungal drug in the pharmaceutical composition for nail is decided depending on the type of the antifungal drug and may ordinarily be 1 to 10 mass % (hereinafter simply described as %), preferably 1% to 5%, with respect to a total of the pharmaceutical composition for nail.

Examples of alkylpyrrolidone or the derivative thereof (hereinafter referred to as alkylpyrrolidone or the like) to be used for the pharmaceutical composition for nail of this invention include one or more alkylpyrrolidone or the like selected from N-methyl-2-pyrrolidone, N-(2-hydroxyethyl) pyrrolidone, N-octylpyrrolidone, N-vinyl-2-pyrrolidone, 2-pyrrolidone, and 3-pyrrolidone or derivatives thereof. Among these alkylpyrrolidone or the like, N-methyl-2-pyrrolidone that enhances the permeability to nail is preferred.

A content of the alkylpyrrolidone or the like in the pharmaceutical composition for nail may preferably be 1% to 20%, more preferably 1% to 10%. The solubility can be reduced when the content is less than the above-specified range particularly in the case of containing the slightly water-soluble antifungal drug, while stability of the preparation can be deteriorated when the content exceeds the above-specified range.

The crosslinking hydrogel that is the remaining one of the essential ingredients of the pharmaceutical composition for nail of this invention is obtainable by crosslinking a water-soluble crosslinking polymer by using a crosslinking agent in the presence of a water. The water-soluble crosslinking polymer is a water-soluble polymer that is gelled through crosslinking with a crosslinking agent.

Examples of the water-soluble crosslinking polymer to be crosslinked include one or more water-soluble crosslinking polymers selected from partially neutralized polyacrylate (a sodium content is 10% to 19%, for example), polyacrylic acid, sodium polyacrylate, carboxymethyl cellulose sodium, gelatin, and the like. Among these water-soluble crosslinking polymers, polyacrylic acid and/or partially neutralized polyacrylate are preferred. A content of the water-soluble crosslinking polymer in the pharmaceutical composition for nail is appropriately decided depending on solubility to water, reactivity to crosslinking agent (particularly aluminum compound) described later in this specification, and adhesiveness when adhered to the nail and may preferably be 1% to 30%, more preferably 1% to 20%. An adhesion property to nail of the preparation can be deteriorated when the content is less than the above-specified range, and releasability from nail can be deteriorated when the content exceeds the above-specified range.

Examples of the crosslinking agent for forming the crosslinking hydrogel by crosslinking the water-soluble crosslinking polymer include salts of various polyvalent metals such as an aluminum compound, a magnesium compound, and a calcium compound, and it is possible to use a compound having two or more epoxy groups in one molecule and the like. A content of the crosslinking agent in the pharmaceutical composition for nail may preferably be 0.1% to 1%, more preferably 0.1% to 0.5%.

A content of the water in the pharmaceutical composition for nail required for obtaining the crosslinking hydrogel may preferably be 20% to 80%, more preferably 30% to 50%.

Also, a polyvalent alcohol may be contained in the pharmaceutical composition for nail as a solubilizer (an auxiliary solubilizer) for the antifungal drug. Examples of the polyvalent alcohol include one or more polyvalent alcohols selected from glycols such as polyethyleneglycol and propyleneglycol, glycerin, diglycerin, and sorbitol. Preferred among the above are glycols, and specific examples thereof include polyethyleneglycol having an average molecular weight of 200, 300, 400, 600, 1000, 1500, 1540, 4000, 6000, 20000, or 35000, propyleneglycol, dipropyleneglycol, polypropyleneglycol, 1,3-butyleneglycol, 1,4-butyleneglycol, isobutyleneglycol, and the like. Particularly, polyethyleneglycol having the average molecular weight of 200, 300, 400, 600, 1000, or 1500 is preferred. A content of the polyvalent alcohol in the pharmaceutical composition for nail may preferably be 1% to 50%, more preferably 20% to 50%.

Further, an adhesion enhancer having an adhesion enhancing action though not crosslinked by the crosslinking agent may be added on top of the above-described ingredients. Examples of such adhesion enhancer include starch acrylate, polyvinyl alcohol, a carboxyvinyl polymer, hydroxypropyl cellulose, carboxymethyl cellulose, casein sodium, hydroxymethyl cellulose, hydroxyethyl cellulose, hydroxypropylmethyl cellulose, methyl cellulose, polyvinyl pyrrolidone, sodium alginate, a methylvinylether-maleic anhydride copolymer, and the like, and these adhesion enhancers may be used alone or in combination of two or more. Among these adhesion enhancers, carboxymethyl cellulose and/or hydroxypropyl cellulose are/is preferred, and, particularly in the case of using polyacrylic acid and/or partially neutralized polyacrylate as the water-soluble crosslinking polymer, carboxymethyl cellulose and/or hydroxypropyl cellulose are/is preferred since the combination contributes to good shaping property. A content of the adhesive enhancer in the pharmaceutical composition for nail may preferably be 1% to 10%, more preferably 1% to 5%.

Further, various arbitrary ingredients such as a pH adjusting agent, a moisturizer, a thickener, a moisture adjuster, an absorption enhancer, a surfactant, a preservative, an antioxidant, and a perfume may be added to the pharmaceutical composition for nail of this invention when so required.

As the pH adjusting agent, organic acid such as lactic acid, citric acid, malic acid, tartaric acid, oxalic acid, benzoic acid, glycolic acid, acetic acid, propionic acid, succinic acid, and malonic acid may be used. These pH adjusting agents may be used alone or in combination of two or more. These pH adjusting agents may be so added as to keep a pH value of the base to 3.5 to 6.5 from the view point of stability of the preparation.

Examples of the thickener include a powdered acacia, dextrin, powdered tragacanth, pectin, a xanthan gum, glycerin, talc, and the like.

Examples of the moisture adjuster include light anhydrous silicic acid, sodium dl-pyrrolidone carboxylate, and the like.

Examples of the absorption enhancer include urea, dimethylsulfoxide, ethyleneglycol salicylate, crotamiton, benzylalcohol, isopropyl myristate, and the like.

Examples of the surfactant include polysorbate, a polyoxyethylene hydrogenated caster oil, sucrose esters fatty acids, sodium lauryl sulfate, stearyl alcohol, diethyl sebacate, polyethyleneglycol monostearate, and the like.

The preservative, the antioxidant, and the perfume may appropriately be contained within the range that does not impair the effect of this invention.

It is possible to produce the pharmaceutical composition for nail of this invention by dissolving or dispersing the essential ingredients, i.e. the antifungal drug, the alkylpyrrolidone, the water-soluble crosslinking polymer, the crosslinking agent, and the water forming the crosslinking hydrogel, and the arbitrary ingredients described above, followed by mixing. More specifically, production is performed by: adding the arbitrary ingredients to the antifungal drug, the alkylpyrrolidone, the water-soluble crosslinking polymer, the crosslinking agent, and the water; sufficiently mixing the ingredients, adding the pH adjusting agent to the mixture; and sufficiently mixing again.

In the production of the pharmaceutical composition for nail, the antifungal drug which is a medical agent may preferably be dissolved in advance to be used for the production. More specifically, it is preferable to perform the production by: dissolving the antifungal drug into the alkylpyrrolidone; adding other ingredients, followed by sufficient mixing; and adding the pH adjusting agent, followed by sufficient mixing again.

The pharmaceutical composition for nail to be obtained as described above may be formulated into a gel, a cream, an ointment, a liquid, a lotion, an emulsion, an adhesive patch, and the like. Among the above formulations, the adhesive patch is preferred.

More specifically, in order to obtain the adhesive patch from the pharmaceutical composition for nail of this invention, the pharmaceutical composition for nail of this invention is applied and spread on an appropriate support by using an extension machine, for example, and then a releasable liner or the like is attached to an application surface as required, followed by stamping out into the size for attachment to nail with the use of a metal die. Further, it is preferable to provide the adhesive patch with a cover sheet having an adhesive layer for the purpose of enhancing a fixing property to the application part (affected area) on a surface of the support reverse to the surface on which the pharmaceutical composition for nail is applied and spread.

As the support on which the pharmaceutical composition for nail is applied and spread may preferably be those that do not exert any influence on discharge of the drug, and both of an elastic support and a non-elastic support are usable. Since the support is required to tightly seal the nail in order to improve the permeability to nail, it is preferable to use a water-impermeable material for the support. Specific examples of the support include a non-woven cloth, a cloth, a film (including a sheet), a porous body, a foamed body, a paper, a laminated body obtainable by laminating a film on a non-woven cloth or a cloth, and the like. Examples of the materials for the support include a non-woven cloth (synthetic cloth), staple fiber muslin, a vinylchloride film, a polyethylene film, a polyurethane-vinylchloride copolymer film, a polyurethane film, a polypropylene film, a polyester film, a polyethylenetelephthalate separator (PET), cellulose acetate, ethylcellulose, a plastic vinyl acetate-vinylchloride copolymer, nylon, an ethylene-vinyl acetate copolymer, a plastic polyvinylchloride, polyvinylidene chloride, aluminum, and the like.

As the liner for covering the pharmaceutical composition for nail, it is preferable to use a water-impermeable material in view of the necessity of preventing evaporation of moisture from the pharmaceutical composition for nail. Specific examples of such material include a film (including a sheet), a porous body, a foamed body, and the like. Examples of the materials for the liner include staple fiber muslin, a vinylchloride film, a polyethylene film, a polyurethane-vinylchloride copolymer film, a polyurethane film, a polypropylene film, a polyester film, a polyethylenetelephthalate separator (PET), cellulose acetate, ethylcellulose, a plastic vinyl acetate-vinylchloride copolymer, nylon, an ethylene-vinyl acetate copolymer, a plastic polyvinyl chloride, polyvinylidene chloride, a releasable paper (exfoliate paper), and the like. Further, in order to adjust the releasability, embossing, a silicone treatment, a Colona treatment, or the like may be performed.

Examples of a material for the cover sheet to be provided on the support on which the pharmaceutical composition for nail is applied and spread include a non-woven cloth, a cloth, a net, a knit, a gauze, a film, and the like, and those having a certain degree of air permeability is preferred in view of prevention of steaming and rash at the fixing part. Specific examples of the materials for the cover sheet include polyester (fiber), polyethylene (fiber), polypropylene (fiber), rayon, cupra, hemp, and the like. Examples of an adhesive to be used for the adhesive layer of the cover sheet include an acryl-based adhesive such as alkylester acrylate, a rubber-based adhesive such as an S-I-S copolymer, a silicon-based adhesive, and the like.

The pharmaceutical composition for nail of this invention obtained as described above is excellent in drug-permeability to nail and capable of fully exhibiting effects of the antifungal drug. Therefore, the pharmaceutical composition for nail of this invention is suitably used for a treatment of diseases such as nail tinea and nail candidiasis of fingers or toes, particularly for treatment of nail tinea wherein nails of fingers or toes are infected with fungus. More specifically, in the case of using the adhesive patch using the pharmaceutical composition for nail of this invention for treatment of nail mycosis, one to four patches may preferably be attached to an affected area such as a hand and a foot per day.

EXAMPLES

Hereinafter, this invention will be described in more details in conjunction with examples and test examples, and this invention is not at all limited by the examples.

Example 1

Production of Pharmaceutical Composition for Nail (1)

The pharmaceutical composition for nail of this invention was produced on the prescription of Table 1 by employing the production method described below.
(Production Method)

Lanoconazole was dissolved into N-methyl-2-pyrrolidone, and polyethyleneglycol and propyleneglycol were added thereto, followed by adding partially neutralized polyacrylate, a dried aluminum hydroxide gel, and light anhydrous silicic acid, followed by sufficient stirring for dispersion.

An aqueous solution that had been obtained by dissolving polyvinylalcohol into a half of a purified water was added to the dispersion liquid by small amounts, followed by sufficient mixing. Lactic acid dissolved into the rest of the purified water was added to the mixture by small amounts, followed by sufficient mixing for crosslinking, thereby obtaining the pharmaceutical composition for nail.

100 g/m² of the thus-obtained pharmaceutical composition for nail was applied and spread on a non-woven cloth used as a support by using a spatula, followed by covering with a polypropylene film. The non-woven cloth was cut into an appropriate size, followed by stamping out into the size for attachment to nail with the use of metal die, thereby obtaining an adhesive patch type pharmaceutical composition for nail (Invention Product 1).

Example 2

Production of Pharmaceutical Composition for Nail (2)

An adhesive patch type pharmaceutical composition for nail (Invention Product 2) was produced on the prescription of Table 1 in the same manner as in Example 1 except for using clotrimazole and a carboxyvinyl polymer in place of lanoconazole and polyvinyl alcohol.

Example 3

Production of Pharmaceutical Composition for Nail (3)

An adhesive patch type pharmaceutical composition for nail (Invention Product 3) was produced on the prescription of Table 1 in the same manner as in Example 1 except for using bifonazole in place of lanoconazole and adding glycerin. In addition, the glycerin is added together with the propylene glycol.

Comparative Example 1

Production of Comparative Pharmaceutical Composition for Nail

An adhesive patch type comparative pharmaceutical composition for nail (Comparative Product 1) was produced on the prescription of Table 1 by an ordinary method.

The prescriptions of the Invention Products 1 to 3 and the Comparative Product 1 are shown in Table 1.
(Prescriptions)

TABLE 1

| Ingredients (mass %) | Invention Product 1 | Invention Product 2 | Invention Product 3 | Comparative Product 1 |
|---|---|---|---|---|
| 1 Lanoconazole | 1 | — | — | 1 |
| 2 Clotrimazole | — | 1 | — | — |
| 3 Bifonazole | — | — | 1 | — |
| 4 N-methyl-2-pyrrolidone | 8 | 5 | 10 | — |
| 5 Polyethyleneglycol (average molecular weight: 400) | 27 | 25 | 20 | 4 |
| 6 Glycerin | — | — | 5 | 40 |
| 7 Propyleneglycol | 10 | 15 | 10 | — |
| 8 Partially neutralized polyacrylate | 1.92 | 2.4 | 3.6 | — |
| 9 Polyvinyl alcohol | 3.5 | — | 3.0 | — |
| 10 Carboxyvinyl polymer | — | 0.5 | — | — |
| 11 Dried aluminum hydroxide gel | 0.3 | 0.3 | 0.3 | — |
| 12 Light anhydrous silicic acid | 1 | 1 | 1 | — |
| 13 Lactic acid | 2 | 2 | 2 | — |
| 14 Purified water | 45.28 | 47.8 | 44.1 | 10 |
| 15 Gelatin | — | — | — | 5 |
| 16 Kaolin | — | — | — | 40 |

Test Example 1

Test on Permeability to Nail Plate Using Cow Hoof

Permeability to nail of the antifungal drug (lanoconazole) of Product 1 of this invention and Comparative Product 1 was evaluated by using a cow hoof. The test was conducted by: slicing the cow hoof into slices each having a thickness of about 1.0 mm; placing the slice in a Franz cell; each of test samples of Invention Product 1 and Comparative Product 1 was placed on an upper part of the slice; pouring an isotonic phosphate buffer solution (pH 7.4) into a reservoir; and sampling 1.5 mL of the buffer solution at every sampling time to measure an amount of the antifungal drug in the sampled buffer solution. Quantitative determination of the antifungal drug amount was performed by using a high performance liquid chromatography (HPLC) (HPLC Isocratic System: product of JASCO Corporation). A relationship between an accumulated amount of the antifungal drug permeated through nail plate and elapsed time from the start of test to 32 hours after the start of test is shown in FIG. 1.

As shown in FIG. 1, since the pharmaceutical composition for nail of Invention Product 1 was increased in accumulated amount of the permeated antifungal drug over time, it was confirmed that the antifungal drug was permeated into the nail plate over time. On the other hand, only slightest change was observed in the accumulated amount of permeated antifungal drug with time of the adhesive patch of Comparative Product 1.

Test Example 2

Measurement of Concentration of Antifungal Drug in Nail Plate

Each of the test samples of Product 1 of this invention and Comparative Product 1 was removed from a surface of the cow hoof slice after the termination of the test for permeability to nail of Test Example 1 (after 32 hours had passed) and perfectly wiped off from the surface with ethanol and water. Each of the samples was placed in an isotonic phosphate buffer solution (pH: 7.4), and shaking extraction was performed for 24 hours by using WATER BATH SHAKER (PERSONAL-11: product of TAITEC). The sample was taken out from the buffer solution, and another extraction operation was performed in the same manner. The thus obtained extract liquids were mixed, and the antifungal drug in the extract was analyzed by quantitative determination by HPCL in the same manner as in Test Example 1. Results are shown in Table 2.

(Results)

TABLE 2

|  | Concentration in Nail Plate (µg/g of nail) |
|---|---|
| Invention Product 1 | 34.21 |
| Comparative Product 1 | 9.31 |

As is indicated by results of Table 2, it was confirmed that the permeated amount of the antifungal drug in the nail plate in the case of using the pharmaceutical composition for nail of Invention Product 1 was larger than that in the case of using Comparative Product 1.

Test Example 3

Evaluation of Antifungal Drug Stability in Long Term Storage

The pharmaceutical composition for nail of Invention Product 1 was evaluated by way of stabilities of the antifungal drug (lanoconazole) in one-month storage and two-month storage at 50° C. by using a residual ratio immediately after the production as 100%. Results are shown in Table 3.

(Results)

TABLE 3

|  | Retention (%) |
|---|---|
| Immediately after production | 100.1 |
| One month after production | 98.8 |
| Two months after production | 96.3 |

As is indicated by the result of Table 3, the antifungal drug in the pharmaceutical composition for nail of this invention was retained at a substantially same level with that of immediately after the production in the long term storage, and it was confirmed that the pharmaceutical composition for nail of this invention is capable of stably retaining the antifungal drug in the long term storage.

Example 4

Production of Pharmaceutical Composition for Nail (4)

Pharmaceutical compositions for nail of this invention (Invention products 4 and 5) were produced on the prescription of Table 4 by employing the production method described below.

(Production Method)

Lanoconazole dissolved into the mixture of N-methyl-2-pyrrolidone and polyethyleneglycol, a part of a water-soluble polymer, and glycerin were dissolved into a part of a purified water, and other ingredients of the composition were added thereto, followed by sufficient mixing. Other ingredients were further added thereto, followed by mixing. Lastly, the rest of the purified water and partially neutralized polyacrylate were added, followed by further mixing until obtaining a uniform mixture, thereby obtaining a plaster. The plaster was uniformly spread and placed on a non-woven cloth, and the non-woven cloth was shaped into a predetermined shape, followed by packaging to obtain an adhesive patch.

TABLE 4

|  |  | Invention Product | |
|---|---|---|---|
| Ingredients (mass %) |  | 4 | 5 |
| 1 | Lanoconazole | 1 | 4 |
| 2 | N-methyl-2-pyrrolidone | 8 | 8 |
| 3 | Polyethyleneglycol (average molecular weight: 400) | 10 | 10 |
| 4 | partially neutralized polyacrylate | 4.5 | 4.5 |
| 5 | Polyacrylic acid aqueous solution (20%) | 15 | 15 |
| 6 | Carboxymethyl cellulose sodium | 4.0 | 4.0 |
| 7 | Hydroxypropyl cellulose | 2 | 2 |
| 8 | Aluminum glycinate | 0.2 | 0.2 |
| 9 | Edetate sodium | 0.1 | 0.1 |
| 10 | Glycerin | 30 | 30 |
| 11 | Tartaric acid | 0.5 | 0.5 |
| 12 | Caster oil | 0.5 | 0.5 |
| 13 | Polysorbate | 0.5 | 0.5 |
| 14 | Purified water | 23.8 | 20.8 |

The test for permeability to nail plate using cow hoof of Test Example 1 was performed on the Invention Products obtained as described above, and the products achieved an increase with time in accumulated amount of the permeated antifungal drug as shown in FIG. 1, thereby proving that the products enable the antifungal drug to be permeated into the nail plate over time.

Example 5

Production of Pharmaceutical Composition for Nail (5)

A pharmaceutical composition for nail with a cover sheet (Invention Product 6) was obtained by attaching the non-woven cloth side of the pharmaceutical composition for nail of Invention Product 5 to the center of an adhesive layer of the cover sheet wherein an acryl-based adhesive agent mainly containing 2-ethylhexyl acrylate was applied as the adhesive layer on the whole part of polyester (fiber) having a length of 22 mm and a width of 75 mm.

Test Example 4

Adhesion Test Using Pharmaceutical Composition for Nail and Pharmaceutical Composition for Nail with Cover Sheet For the purpose of confirming an effect of the cover sheet, a test on volunteers was performed by using the pharmaceutical composition for nail of Invention Product 5 and the pharmaceutical composition for nail with cover sheet of Invention Product 6 under the following test conditions. Also, an evaluation of adhesion property after the test was performed under the following standard. Results are shown in Table 5.

<Test Conditions>

Number of Subjects for Nails of Feet: 5
Number of Subjects for Nails of Hands: 4
Test Preparation Invention Product 5 (without cover sheet)
Test Preparation Invention Product 6 (with cover sheet)
Adhered Area Feet (nails of right and left thumbs)
Hand (nails of right and left thumbs)
Adhered Time: about 8 hours <Evaluation Standard>

| Contents | Evaluation | Point |
| --- | --- | --- |
| Perfect adhesion | ◎ | 3 |
| Partial detachment | ○ | 2 |
| Half detachment | Δ | 1 |
| Detached | X | 0 |

TABLE 5

| Invention Product | Adhered Part | Subject | Adhesion Property | Point |
| --- | --- | --- | --- | --- |
| 5 | Thumb of left foot | A | Δ | 1 |
| " | " | B | X | 0 |
| " | " | C | ○ | 2 |
| " | " | D | X | 0 |
| " | " | E | X | 0 |
| " | Thumb of right foot | A | X | 0 |
| " | " | B | X | 0 |
| " | " | C | ○ | 2 |
| " | " | D | X | 0 |
| " | " | E | X | 0 |
| | | | Average point | 0.50 |
| 5 | Thumb of left hand | A | Δ | 1 |
| " | " | B | ○ | 2 |
| " | " | C | ◎ | 3 |
| " | " | D | ○ | 2 |
| " | Thumb of right hand | A | ◎ | 1 |
| " | " | B | ○ | 2 |
| " | " | C | ◎ | 3 |
| " | " | D | ○ | 2 |
| | | | Average point | 2.00 |
| 6 | Thumb of left foot | A | ◎ | 3 |
| " | " | B | ◎ | 3 |
| " | " | C | ◎ | 3 |
| " | " | D | ◎ | 3 |
| " | " | E | ◎ | 3 |
| " | Thumb of right foot | A | ◎ | 3 |
| " | " | B | ◎ | 3 |
| " | " | C | ◎ | 3 |
| " | " | D | ◎ | 3 |
| " | " | E | ◎ | 3 |
| | | | Average point | 3.00 |
| 6 | Thumb of left hand | A | ◎ | 3 |
| " | " | B | ◎ | 3 |
| " | " | C | ◎ | 3 |
| " | " | D | ◎ | 3 |
| " | Thumb of right hand | A | ◎ | 3 |
| " | " | B | ◎ | 3 |
| " | " | C | ◎ | 3 |
| " | " | D | ◎ | 3 |
| | | | Average point | 3.00 |

From Table 5, it is indicated that Invention Product 5 has a certain degree of adhesion property and is not detached during sleep when attached to the nails of fingers. However, it is indicated that Invention Product 5 can be detached by contact with bedclothes in the case of the nails of feet. Invention Product 6 was not detached in both of hands and feet during sleep, and the preparations were tightly fixed to the affected areas, so that Invention Product 6 is expected to achieve a satisfactory treatment effect.

INDUSTRIAL APPLICABILITY

The pharmaceutical composition for nail of this invention is capable of enhancing drug-permeability to nail and fully exhibiting the effects of an antifungal drug.

Therefore, the pharmaceutical composition for nail of this invention is expected to be used as an external preparation effective for treatment of nail diseases such as nail tinea.

DESCRIPTION OF REFERENCES AND SIGNS

Figure 1:
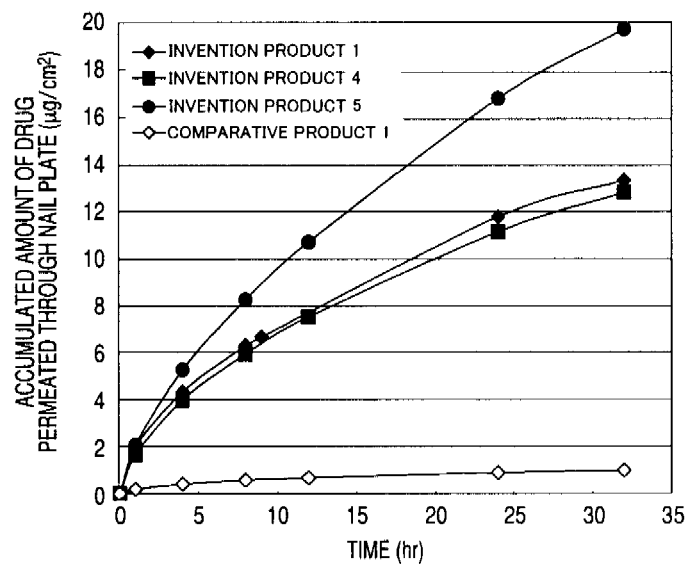
FIG. 1 A diagram showing a relationship between an elapsed time and an accumulated amount of an antifungal drug permeated into the nail plate.
Figure 2:
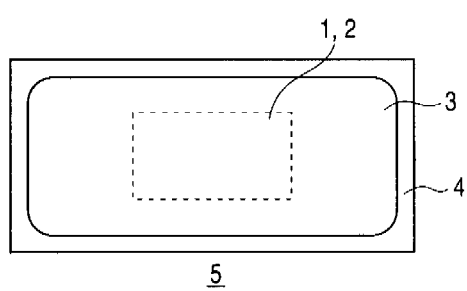
FIG. 2 One example of a plan view of an adhesive patch for nail of this invention with a cover sheet.
Figure 3:
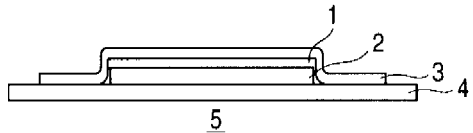
FIG. 3 One example of a sectional view of the adhesive patch for nail of this invention with a cover sheet.
Figure 4:
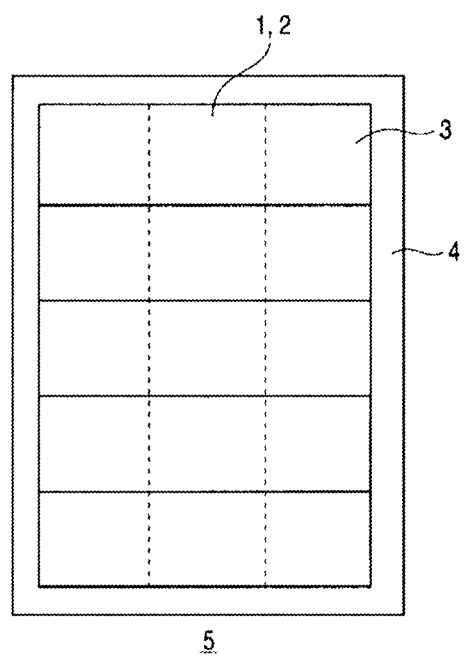
FIG. 4 One example of a plan view of the adhesive patch for nail in the form of a sheet of this invention with a cover sheet.

1: support
2: adhesive layer
3: cover sheet
4: liner
5: pharmaceutical composition for nail

The invention claimed is:
1. A pharmaceutical composition for nail consisting of an antifungal drug, alkylpyrrolidone or a derivative thereof, and a single crosslinking hydrogel,
    wherein the antifungal drug is one or more selected from the group consisting of lanoconazole, clotrimazole, and bifonazole, and a content of the antifungal drug in the pharmaceutical composition is 1 to 5%,
    the alkylpyrrolidone is N-methyl-2-pyrrolidone and a content of the alkylpyrrolidone in the pharmaceutical composition is 1 to 20%,
    the single crosslinking hydrogel consists of 1 to 30% of a water-soluble crosslinking polymer, 1 to 50% of a polyvalent alcohol, 1 to 10% of an adhesion enhancer, 0.1 to 1% of a crosslinking agent, and 20 to 80% of water, and
    the pharmaceutical composition further comprises one or more ingredients selected from the group consisting of a pH adjusting agent, a thickener, a moisture adjuster, an absorption enhancer, and a surfactant.
2. The pharmaceutical composition for nail according to claim 1, wherein the water-soluble crosslinking polymer is one or more selected from the group consisting of partially neutralized polyacrylate, polyacrylic acid, and carboxymethyl cellulose sodium,
    the polyvalent alcohol is one or more selected from the group consisting of glycols such as polyethyleneglycol and propyleneglycol, and glycerin,
    the adhesion enhancer is one or more selected from the group consisting of polyvinyl alcohol, a carboxyvinyl polymer, and hydroxypropyl cellulose, and
    the crosslinking agent is one or more selected from the group consisting of salts of a polyvalent aluminum, magnesium, or calcium compound, dried aluminum hydroxide gel, and glycinal.

* * * * *